United States Patent
Park et al.

(10) Patent No.: US 10,744,042 B2
(45) Date of Patent: Aug. 18, 2020

(54) SMART INFANT TOILET SYSTEM AND METHOD THEREOF

(71) Applicant: MONIT CORP., Seoul (KR)

(72) Inventors: Dohyeong Park, Seoul (KR); Jae Ho Baek, Seoul (KR); Jung Hun Lee, Gyeonggi-do (KR); Yeo Hwan Yoon, Seoul (KR); Seong Cheol Lim, Gyeonggi-do (KR); Ju Ho Kim, Gyeonggi-do (KR); Ja Young Moon, Gyeonggi-do (KR); Hye Bin Lee, Gyeonggi-do (KR)

(73) Assignee: MONIT CORP., Seoul (KR)

( * ) Notice: Subject to any disclaimer, the term of this patent is extended or adjusted under 35 U.S.C. 154(b) by 0 days.

(21) Appl. No.: 15/573,883

(22) PCT Filed: Jul. 18, 2017

(86) PCT No.: PCT/KR2017/007728
§ 371 (c)(1),
(2) Date: Aug. 21, 2019

(87) PCT Pub. No.: WO2018/216848
PCT Pub. Date: Nov. 29, 2018

(65) Prior Publication Data
US 2019/0365572 A1    Dec. 5, 2019

(30) Foreign Application Priority Data
May 22, 2017   (KR) .................. 10-2017-0062747

(51) Int. Cl.
*G08B 23/00*   (2006.01)
*A61F 13/42*   (2006.01)
(Continued)

(52) U.S. Cl.
CPC ............. *A61F 13/42* (2013.01); *G01D 21/02* (2013.01); *G08B 21/20* (2013.01); *A47K 11/04* (2013.01);
(Continued)

(58) Field of Classification Search
CPC ....... A61F 13/42; A47K 11/06; G08B 21/201; G08B 21/0211
See application file for complete search history.

(56) References Cited

U.S. PATENT DOCUMENTS 9,545,342 B2 *   1/2017   Cretu-Petra ............. A61F 13/42
10,076,214 B2 *   9/2018   Goh Aow ............... A47K 3/127
(Continued)

FOREIGN PATENT DOCUMENTS

JP    2017-081401    5/2017
KR    10-2014-0039941    4/2014
(Continued)

OTHER PUBLICATIONS

International Search Report dated Feb. 14, 2018 for PCT/KR2017/007728.

*Primary Examiner* — Toan N Pham

(57) ABSTRACT

The present invention relates to a smart infant toilet system and a method thereof, and the system includes a first sensor mounted to an infant product to sense external temperature and humidity, a second sensor mounted to the infant product to sense gas, third sensor mounted to the infant product to sense whether an infant rides on the infant product, a control module configured to set critical temperature and humidity, and an alarming unit configured to provide an alarm to a guardian when it is determined that the comparative temperature and humidity are out of the preset range of the critical temperature and humidity.

9 Claims, 1 Drawing Sheet

(51) Int. Cl.
*G01D 21/02* (2006.01)
*G08B 21/20* (2006.01)
*A47K 11/04* (2006.01)
*A47K 11/06* (2006.01)

(52) U.S. Cl.
CPC ......... *A47K 11/06* (2013.01); *A61F 2013/421* (2013.01); *A61F 2013/424* (2013.01)

(56) References Cited

U.S. PATENT DOCUMENTS

| | | |
|---|---|---|
| 10,571,470 B2 * | 2/2020 | Hasegawa ............ A61B 5/0004 |
| 2016/0000378 A1 * | 1/2016 | Hall ................... A61B 5/14532 |
| | | 702/19 |
| 2017/0035622 A1 | 2/2017 | Wang |
| 2018/0303466 A1 * | 10/2018 | Kashyap ................. E03D 11/13 |

FOREIGN PATENT DOCUMENTS

| | | |
|---|---|---|
| KR | 10-2016-0133588 | 11/2016 |
| KR | 10-1705278 | 11/2016 |
| KR | 10-1681514 | 12/2016 |
| KR | 10-2017-0038552 | 4/2017 |

* cited by examiner

SMART INFANT TOILET SYSTEM AND METHOD THEREOF

This application claims the priority of Korean Patent Application No. 10-2017-0062747, filed on May 22, 2017 in the KIPO (Korean Intellectual Property Office), the disclosure of which is incorporated herein entirely by reference. Further, this application is the National Stage application of International Application No. PCT/KR2017/007728, filed Jul. 18, 2017, which designates the United States and was published in Korean. Each of these applications is hereby incorporated by reference in their entirety into the present application.

TECHNICAL FIELD

This disclosure relates to relates to a smart infant toilet system and a method thereof, and more particularly, to a smart infant toilet system which includes a plurality of sensors disposed at an infant product and senses temperature, humidity and gas by using the sensors to check whether the infant has discharged an excretion and whether the excretion is urination or defecation and give an alarm to a guardian in real time, and a method thereof.

BACKGROUND ART

Generally, infants are under the age of 3 or less need someone's help. Because of this, it is necessary for an infant keeper such as a mother to always take care of the infant in a safe and healthy manner near the infant.

In particular, infants under the age of 3 or less cannot control themselves when discharging an excretion and thus use diaper products. When discharging an excretion, a diaper-wearing infant is crying due to the feeling at the skin to notify inconvenience to the infant keeper so that the infant keeper exchanges the diaper.

However, when taking care of an infant, it is not possible for the infant keeper to be always near the infant, and even though the infant keeper is near the infant, if the infant does not respond to the defecation, the infant keeper cannot notice this. Thus, the infant keeper should touch the diaper frequently for checking. In addition, if the infant keeper does not immediately replace the diaper when the infant has discharged urination or defecation, it is impossible to prevent the discomfort caused by the diaper wetting and the disease caused by the erosion of the buttocks.

In order to solve such a problem, Korean Unexamined Patent No. 10-2014-0039941 discloses a diaper having an excretion detecting function. When an infant uses the diaper having an excretion detecting function, it is easy to check whether the infant has discharged urination or defecation by checking a discoloration sheet.

However, if the infant wears a baby sling, it is inconvenient to unfasten the baby sling in order to check whether the infant has discharged urination or defecation, and such a diaper is generally more expensive than a general diaper.

Meanwhile, Korean Patent Registration No. 10-1705278 discloses a smart Internet-based smart diaper management system. In Korean Patent Registration No. 10-1705278, it is possible to detect whether a diaper is changed by checking an amount of current flowing through the diaper by means of a capacitance sensor or the like, and thus it is possible to check whether the infant has discharged urination or defecation on the diaper. However, in the disclosed patent, it is impossible to set an initial value according to the weather condition, and thus the change of the environment caused by the change of climate or area cannot be reflected. Thus, it is substantially impossible to accurately recognize whether the infant has discharged urination or defecation.

DISCLOSURE OF THE INVENTION

Technical Problem

This disclosure is directed to providing a smart infant toilet system, which includes a plurality of sensors disposed at an infant product and senses temperature, humidity and gas by using the sensors to check whether the infant has discharged an excretion and whether the excretion is urination or defecation and give an alarm to a guardian in real time, and a method thereof.

The object of the present disclosure is not limited to the above, and other objects not mentioned can be clearly understood by those skilled in the art from the description below.

Technical Solution

In one general aspect of the present disclosure, there is provided a smart infant toilet system, comprising: a first sensor mounted to an infant product to sense external temperature and humidity; a second sensor mounted to the infant product to sense gas; a third sensor mounted to the infant product to sense whether an infant rides on the infant product; a control module configured to set critical temperature and humidity as temperature and humidity sensed by the first sensor before the infant rides, sense temperature and humidity at regular time intervals by the first sensor after the infant rides to generate comparative temperature and humidity, determine whether the comparative temperature and humidity are out of a preset range of the critical temperature and humidity, and classify a state of an excretion of the infant into urination or defecation by the second sensor; and an alarming unit configured to provide an alarm to a guardian when the comparative temperature and humidity are out of the preset range of the critical temperature and humidity and thus it is determined that the infant has discharged urination or defecation.

In this embodiment, the second sensor may be a VOC sensor for sensing gas generated when the infant discharges urination or defecation.

In this embodiment, the smart infant toilet system may further include a fourth sensor configured to sense heartbeat and breathing of the infant.

In this embodiment, the first sensor may be a temperature and humidity sensor and is disposed at the infant product in a region corresponding to the buttocks of infant, the third sensor may be any one of a capacitive sensor, a resistive sensor, a displacement sensor and an acceleration sensor, and the fourth sensor may be any one of a microwave sensor, a motion sensor and a piezo sensor, capable of sensing heartbeat and breathing of the infant.

In this embodiment, the infant product may be any one of a diaper, a baby sling, a baby stroller and a car seat.

In this embodiment, at least one of the first to fourth sensors may further include a reference setting button for setting an initial reference value in consideration of a state of the infant by a user.

In another aspect of the present disclosure, there is also provided an excretion determining method using a smart infant toilet system, comprising: setting critical temperature and humidity serving as a reference by sensing external temperature and humidity by means of a first sensor before an infant rides an infant product; checking whether the infant rides the infant product; sensing temperature and humidity at regular time intervals by means of the first sensor to check comparative temperature and humidity after it is checked that the infant rides; and successively comparing the critical temperature and humidity with the comparative temperature and humidity, and classifying an excretion of the infant into urination or defecation when the comparative temperature and humidity is out of a preset range of the critical temperature and humidity; and determining that the infant has discharged urination or defecation and providing an alarm to a guardian.

Advantageous Effects

The smart infant toilet system according to the present disclosure and its method is possible to sense temperature, humidity and gas by means of sensors and check whether the infant has discharged an excretion and whether the excretion is urination or defecation and give an alarm to a guardian in real time.

The effect of the present disclosure is not limited to the above, and other effects not mentioned can be clearly understood by those skilled in the art from the description below.

MODE FOR CARRYING OUT THE INVENTION

Hereinafter, an embodiment of the present disclosure will be described in detail with reference to the accompanying drawings. At this time, it should be noted that like components are denoted by like reference signs as possible. In addition, any known functions and configurations that may obscure the essence of the present disclosure will not be explained. For the same reason, some components in the accompanying drawings are exaggerated, omitted or schematically shown.

In addition, throughout the specification, when any component is referred to as including another component, it means that the component can include other components further, instead of excluding other components, unless specifically stated otherwise. In addition, throughout the specification, the term "on . . . " means to be located above or below a corresponding portion, and does not necessarily mean that the component is located at an upper side based on the gravitational direction.

Figure 1:
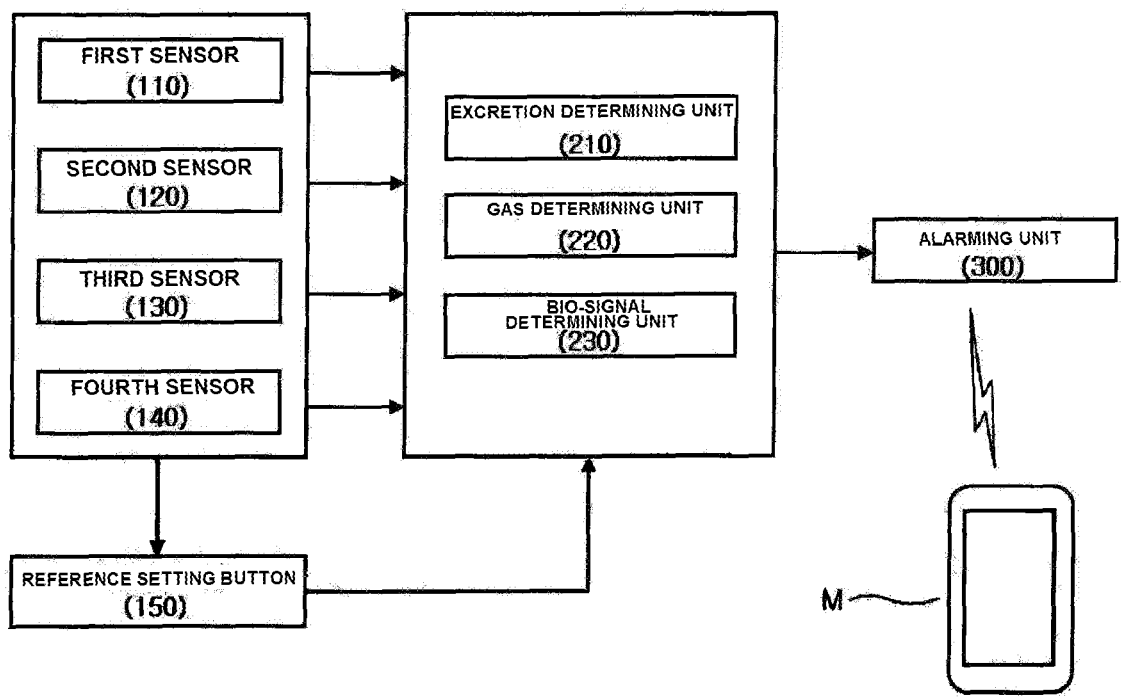
FIG. 1 is a diagram showing a smart infant toilet system according to an embodiment of the present disclosure.

FIG. 1 is a diagram showing a smart infant toilet system according to an embodiment of the present disclosure.

Referring to FIG. 1, the smart infant toilet system according to an embodiment of the present disclosure includes a first sensor 110, a second sensor 120, a third sensor 130, a control module 200 and an alarming unit 300. The first sensor 110, the second sensor 120, the third sensor 130, the microwave sensor 140, the control module 200 and the alarming unit 300 may be mounted to an infant product. Here, the infant product may be any one of a baby sling, a baby stroller and a car seat, and may be applied to various infant products without being limited to the above.

The first sensor 110 is mounted to the infant product to sense external temperature and humidity. At this time, when being disposed at the infant product, the first sensor 110 may be located in a region corresponding to the buttocks of the infant. If the first sensor 110 is located in a region corresponding to the buttocks of the infant as above, the change of humidity generated when the infant discharges urination or defecation may be sensed more accurately.

Thus, the first sensor 110 may set an initial value according to an environmental change in consideration of a climatic condition or a local condition. Therefore, since the initial reference value may be set considering the regional temperature and humidity deviations, it is possible to provide accurate reference values for the change of urination or defecation of the infant.

The second sensor 120 is mounted on the infant product to sense gas. The gas is used to check whether the infant has discharged urination or defecation by sensing an ambient air that changes when the infant discharges urination or defecation. The second sensor 120 is disposed adjacent to the first sensor 110 to more accurately detect the gas generated when the infant discharges urination or defecation. At this time, the second sensor 120 may be provided as a VOC sensor to determine whether the infant has discharged urination or defecation based on the gas generated when the infant discharges urination or defecation.

The third sensor 130 is mounted to the infant product to sense whether the infant rides on the infant product. The third sensor 130 is a capacitive sensor, a resistive sensor, a displacement sensor or an acceleration sensor to check whether the infant rides on the infant product by sensing deformation of the infant product by means of the weight of the infant product generated when the infant rides on the baby sling, baby stroller or the car seat.

The fourth sensor 140 may be any one of a microwave sensor, a motion sensor, and a piezo sensor, which may sense heartbeat and breathing of the infant. The microwave sensor uses the fact that when a microwave signal is reflected on a moving object, the frequency of the signal changes in proportion to the velocity of the object due to the Doppler Effect. In other words, the frequency of a signal reflected from a moving object with a constant period is maintained identically but the phase changes with time. The piezo sensor uses the fact that heartbeat and breathing are sensed by measuring a change of force caused by the heartbeat or breathing and amplifying the same.

By using this method, a state of the infant may be figured out by noninvasively sensing vital signs such as heartbeat and breathing rate through the signals of the infant sensed by the fourth sensor 140. For this, the fourth sensor 140 may be located at a location corresponding to the heart of the infant when disposed at the infant product.

Meanwhile, at least one of the first sensor 110 to the fourth sensor 140 may further include a reference setting button 150 for setting an initial reference value in consideration of a state of the infant by a user. The reference setting button 150 allows the user, namely the parent, to react more precisely to the change of condition of the infant by setting a criterion for which a deviation may occur depending on the state of the infant. On the other hand, the reference setting button 150 may provide a reference of the infant in terms of big data based on the data stored continuously with respect to the state of the infant, and the reference setting button 150 may be directly disposed at the infant product or be provided through a program installed at a smart terminal of the user.

The control module 200 sets critical temperature and humidity based on the temperature and humidity sensed by the first sensor 110 before the infant rides, then senses temperature and humidity at regular time intervals by the first sensor 120 after the infant rides to generate comparative temperature and humidity, determines whether the comparative temperature and humidity are out of a preset range of the critical temperature and humidity, and classifies a state of an excretion into urination or defecation. The control module 200 includes an excretion determining module 210, a gas determining module 220 and a bio-signal determining module 230.

Here, the critical temperature and humidity are used as reference temperature and humidity for checking whether the infant has discharged urination or defecation, and the critical temperature and humidity may be changed depending on a condition of the infant, an ambient environment (weather), a state of the diaper, and a condition of the infant product and is not always set as a fixed value.

The excretion determining module 210 senses temperature and humidity at regular time intervals by means of the first sensor 120 after the infant rides to generate comparative temperature and humidity, and determines whether the comparative temperature and humidity is out of the preset range of the critical temperature and humidity. At this time, if the comparative temperature and humidity are out of the preset range of critical temperature and humidity, it is determined that the infant discharged an excretion.

If it is determined that the infant discharged an excretion, the gas determining module 220 determines whether the infant has discharged urination or defecation based on the sensing value through the second sensor 120. At this time, the guardian may effectively prepare for exchanging the diaper if another alarm is provided to the guardian to classify the excretion into defecation or urination.

For example, if the diaper has good absorbency, there is no problem with the absorbency even though the infant discharges urination more than once, and thus the diaper is frequently used for about two urinations. Thus, if it is checked that the excretion of the infant is urination, the guardian may postpone the replacement of the diaper for a while. However, it may be difficult for the guardian to remember the number of urinations of the infant. Thus, the alarming unit 300 may provide different alarms for the first urination and the second urination in order to prevent the guardian from being confused. This may allow effectively exchange of the diaper and ensure economic efficiency.

If the excretion of the infant is identified as defecation through the gas determining module 220, an alarm may be provided so that the guardian replaces the diaper immediately. In other words, the gas determining module 220 determines whether the excretion is urination or defecation depending on the level of gas according to a preset gas concentration through the second sensor 120.

For example, gases emitting from urination and defecation have different types and concentrations. Unlike urination, defecation is generally smoky. This is because the concentration of hydrogen sulfide and ammonia gas is 1.5 times or more on average. The gas determining module 220 may determine that the excretion is urination if the gas sensed by the second sensor 120 corresponds to a level of 40 to 55%, and determine that the excretion is defecation if the sensed gas corresponds to a level of 60 to 80%. Also, an alar may be provided by the alarming unit 300 based on the above determination.

The bio-signal determining module 230 determines heartbeat and breathing of the infant based on a bio signal of the infant sensed by the microwave sensor 140. In other words, the bio-signal determining module 230 determines whether the infant is awake, is sleeping, or stop breathing due to the infant product or any other reason.

Accordingly, if the intensity of the signal measured from the infant is beyond a preset value and thus it is determined that the infant is in a dangerous state, an alarm is provided to the guardian by the alarming unit 300. At this time, the alarm signal may be simultaneously provided to the alarming unit 300 and a mobile terminal M carried by the guardian. In this case, it is possible to prevent the guardian from failing to receiving the alarm even though the guardian leaves the spot for a moment.

The alarming unit 300 provides an alarm to the guardian if the comparative temperature and humidity are out of the preset range of critical temperature and humidity and thus it is determined that the infant has discharged an excretion. At this time, the alarming unit 300 may provide an alarm through a speaker, and an alarm may be provided to a mobile terminal M of the guardian through a wireless communication module (not shown). Also, the alarming unit 300 may provide different alarms depending on whether the infant has discharged urination or defecation by means of the gas determining module 220.

Figure 2:
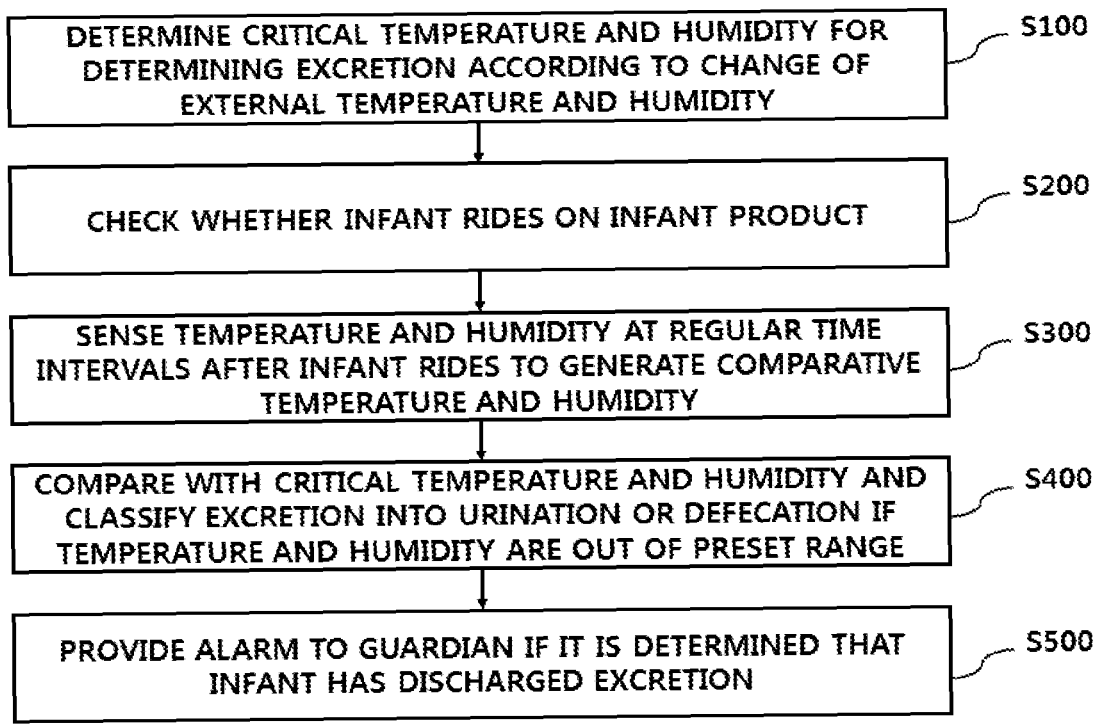
FIG. 2 is a flowchart for illustrating an excretion determining method using the smart infant toilet system according to an embodiment of the present disclosure.

FIG. 2 is a flowchart for illustrating an excretion determining method using the smart infant toilet system according to an embodiment of the present disclosure.

Referring to FIG. 2, an excretion determining method using the smart infant toilet system according to an embodiment of the present disclosure is as follows.

First, in the method using the smart infant toilet system, before an infant rides on an infant product, external temperature and humidity is sensed by the first sensor 110 to set critical temperature and humidity serving as a reference (S100).

It is checked whether the infant rides on the infant product (S200). At this time, whether the infant rides on the infant product may be checked by using a capacitive sensor, a resistance sensor, a displacement sensor or an acceleration sensor, provided at the infant product (S200).

If it is checked that the infant rides, temperature and humidity are sensed at regular time intervals by means of the first sensor 110 to generate comparative temperature and humidity (S300). The humidity gradient sensed at regular time intervals is stored in a storage unit (not shown).

The critical temperature and humidity is continuously compared with the comparative temperature and humidity stored in the storage. If the comparative temperature and humidity are out of the preset range for the critical temperature and humidity, it is determined that the infant has discharged an excretion, and the excretion is classified into urination or defecation (S400). At this time, it is determined whether the excretion is urination or defecation, based on the gas generated from the infant who is wearing the diaper, by means of the second sensor 120.

If it is determined that the infant has discharged an excretion, an alarm is provided to the guardian (S500). Different alarms may be provided depending on whether the excretion is urination or defecation, and also different alarms may be provided depending on whether the urination is discharged once or twice.

Meanwhile, it should be understood that the present disclosure is not intended to limit the scope of the present disclosure, but it is intended merely to easily explain the technique of the present disclosure and to propose specific examples for aiding understanding of the present disclosure. It should be apparent to those skilled in the art that there are many modifications based on the technical idea of the present disclosure other than the embodiments disclosed herein.

The invention claimed is:

1. A smart infant toilet system, comprising:
   a first sensor mounted to an infant product to sense external temperature and humidity;
   a second sensor mounted to the infant product to sense gas;
   a third sensor mounted to the infant product to sense whether an infant rides on the infant product;
   a control module configured to set critical temperature and humidity as temperature and humidity sensed by the first sensor before the infant rides, sense temperature and humidity at regular time intervals by the first sensor after the infant rides to generate comparative temperature and humidity, determine whether the comparative temperature and humidity are out of a preset range of the critical temperature and humidity, and classify a state of an excretion of the infant into urination or defecation by the second sensor; and
   an alarming unit configured to provide an alarm to a guardian when the comparative temperature and humidity are out of the preset range of the critical temperature and humidity and thus it is determined that the infant has discharged urination or defecation.

2. The smart infant toilet system of claim 1, wherein the second sensor is a VOC sensor for sensing gas generated when the infant discharges urination or defecation.

3. The smart infant toilet system of claim 1, further comprising a fourth sensor configured to sense heartbeat and breathing of the infant.

4. The smart infant toilet system of claim 3,
   wherein the first sensor is a temperature and humidity sensor and is disposed at the infant product in a region corresponding to the buttocks of infant,
   wherein the third sensor is any one of a capacitive sensor, a resistive sensor, a displacement sensor and an acceleration sensor, and
   wherein the fourth sensor is any one of a microwave sensor, a motion sensor and a piezo sensor, capable of sensing heartbeat and breathing of the infant.

5. The smart infant toilet system of claim 3,
   wherein at least one of the first to fourth sensors further includes a reference setting button for setting an initial reference value in consideration of a state of the infant by a user.

6. The smart infant toilet system of claim 1,
   wherein the first sensor is a temperature and humidity sensor and is disposed at the infant product in a region corresponding to the buttocks of infant,
   wherein the third sensor is any one of a capacitive sensor, a resistive sensor, a displacement sensor and an acceleration sensor, and
   wherein the fourth sensor is any one of a microwave sensor, a motion sensor and a piezo sensor, capable of sensing heartbeat and breathing of the infant.

7. The smart infant toilet system of claim 1, wherein the infant product is any one of a diaper, a baby sling, a baby stroller and a car seat.

8. The smart infant toilet system of claim 1,
   wherein at least one of the first to fourth sensors further includes a reference setting button for setting an initial reference value in consideration of a state of the infant by a user.

9. An excretion determining method using a smart infant toilet system, comprising:
   setting, by a control module, critical temperature and humidity serving as a reference by sensing external temperature and humidity by means of a first sensor before an infant rides an infant product;
   checking, by the control module, whether the infant rides the infant product;
   sensing, by the control module, temperature and humidity at regular time intervals by means of the first sensor to check comparative temperature and humidity after it is checked that the infant rides;
   successively comparing, by the control module, the critical temperature and humidity with the comparative temperature and humidity, and classifying, by the control module, an excretion of the infant into urination or defecation when the comparative temperature and humidity is out of a preset range of the critical temperature and humidity; and
   determining, by the control module, that the infant has discharged urination or defecation and providing an alarm to a guardian.

* * * * *